United States Patent
Feng et al.

(10) Patent No.: US 11,030,747 B1
(45) Date of Patent: Jun. 8, 2021

(54) SYSTEM AND METHOD FOR AUTOMATIC THORACIC ORGAN SEGMENTATION FROM CT USING A DEEP LEARNING FRAMEWORK

(71) Applicants: Xue Feng, Lexington, KY (US); Quan Chen, Lexington, KY (US)

(72) Inventors: Xue Feng, Lexington, KY (US); Quan Chen, Lexington, KY (US)

( * ) Notice: Subject to any disclaimer, the term of this patent is extended or adjusted under 35 U.S.C. 154(b) by 0 days.

(21) Appl. No.: 16/809,491

(22) Filed: Mar. 4, 2020

(51) Int. Cl.
| | |
|---|---|
| *G06K 9/00* | (2006.01) |
| *G06T 7/00* | (2017.01) |
| *G06T 19/20* | (2011.01) |
| *G06T 7/174* | (2017.01) |
| *G06T 15/08* | (2011.01) |
| *G16H 30/40* | (2018.01) |
| *G16H 20/40* | (2018.01) |
| *G06N 3/08* | (2006.01) |
| *A61N 5/10* | (2006.01) |
| *G06T 11/00* | (2006.01) |

(52) U.S. Cl.
CPC .......... *G06T 7/0014* (2013.01); *A61N 5/1039* (2013.01); *G06N 3/08* (2013.01); *G06T 7/174* (2017.01); *G06T 11/008* (2013.01); *G06T 15/08* (2013.01); *G06T 19/20* (2013.01); *G16H 20/40* (2018.01); *G16H 30/40* (2018.01); *G06T 2207/10081* (2013.01); *G06T 2207/20081* (2013.01); *G06T 2207/20084* (2013.01); *G06T 2207/30012* (2013.01); *G06T 2207/30048* (2013.01); *G06T 2207/30056* (2013.01); *G06T 2207/30061* (2013.01); *G06T 2211/424* (2013.01)

(58) Field of Classification Search
CPC ..... G06T 7/0014; G06T 7/174; G06T 11/008; G06T 15/08; G06T 19/20; G06T 2207/10081; G06T 2207/20081; G06T 2207/20084; G06T 2207/30012; G06T 2207/30048; G06T 2207/30056; G06T 2207/30061; G06T 2211/424; G16H 20/40; G16H 30/40; A61N 5/1039; G06N 3/08

See application file for complete search history.

(56) References Cited

U.S. PATENT DOCUMENTS

| | | | |
|---|---|---|---|
| 2007/0238999 A1* | 10/2007 | Specht | A61B 8/08 600/437 |
| 2020/0143934 A1* | 5/2020 | Gering | G06T 11/60 |
| 2020/0167930 A1* | 5/2020 | Wang | G06T 7/0012 |
| 2020/0211185 A1* | 7/2020 | Hu | G06K 9/6267 |
| 2020/0380696 A1* | 12/2020 | Feng | G06T 7/174 |

* cited by examiner

*Primary Examiner* — Xin Jia (57) ABSTRACT

The present disclosure relates to a method and apparatus for automatic thoracic organ segmentation. The method includes: receiving three-dimensional (3D) images obtained by a computed tomography (CT) system; processing the 3D images to have the same spatial resolution and matrix size; building a two-stage deep learning framework using convolutional neural networks (CNNs) for organ segmentation; adapting the deep learning framework to be compatible with incomplete training data; improving the CNNs upon arrival of new training data; post-processing the output from the deep learning framework to obtain final organ segmentation.

13 Claims, 10 Drawing Sheets

(8 of 10 Drawing Sheet(s) Filed in Color)

SYSTEM AND METHOD FOR AUTOMATIC THORACIC ORGAN SEGMENTATION FROM CT USING A DEEP LEARNING FRAMEWORK

STATEMENT OF GOVERNMENT INTEREST

This invention was made with government support under Grant No. R43EB027523-01A1 awarded by The National Institute of Health. The government has certain rights in the invention.

CROSS-REFERENCE TO RELATED APPLICATION

Not applicable.

FIELD

This disclosure relates to computed tomography (CT) operations that develop and validate a deep learning framework for automatic thoracic organ segmentation.

BACKGROUND

Automatic segmentation of organs from CT images is a key step in radiation treatment planning for cancer patients as it can reduce human efforts and bias. In current clinical practice, the main method of segmenting organs is through manual contouring, which can take 1-2 hours for major thoracic organs due to the large number of axial slices. In addition to time considerations, manual contouring also suffers from inter- and intra-observer variability as well as institutional variability where different sites adopt distinct contouring atlases and labeling criteria. Deep learning framework has shown great success in many medical image segmentation applications but there are still challenges in dealing with large 3D images. In addition, the traditional deep learning framework heavily relies on the size and diversity of the training dataset. However, in practice, the data collection is not finished in one step so that a method to incrementally improve the deep learning models upon the arrival of new dataset is needed.

SUMMARY

Examples of the present disclosure provide a method for automatic segmentation of thoracic organs from CT images in radiation treatment planning using a deep learning framework.

According to a first aspect of the present disclosure, a computer-implemented method for automatic thoracic organ segmentation. The method may include receiving three-dimensional (3D) images obtained by a computed tomography (CT) system, processing the 3D images to have the same spatial resolution and matrix size, building a two-stage deep learning framework based on convolutional neural network (CNN) models for organ segmentation, adapting the deep learning framework to be compatible with incomplete training data, improving the CNN models upon arrival of new training data, and post-processing the output from the deep learning framework to obtain final organ segmentation.

According to a second aspect of the present disclosure, an apparatus for automatic thoracic organ segmentation. The apparatus may include one or more processors, a display, and a non-transitory computer-readable memory storing instructions executable by the one or more processors. Wherein the instructions are configured to receive three-dimensional (3D) images obtained by a computed tomography (CT) system, process the 3D images to have the same spatial resolution and matrix size, build a two-stage deep learning framework based on convolutional neural network (CNN) models for organ segmentation, adapt the deep learning framework to be compatible with incomplete training data, improve the CNN models upon arrival of new training data, and post-process the output from the deep learning framework to obtain final organ segmentation.

According to a third aspect of an example of the present disclosure, a non-transitory computer-readable storage medium having stored therein instructions is provided. When the instructions are executed by one or more processors or one or more graphic processing units of the apparatus, the instructions cause the apparatus to receive three-dimensional (3D) images obtained by a computed tomography (CT) system, process the 3D images to have the same spatial resolution and matrix size, build a two-stage deep learning framework based on convolutional neural network (CNN) models for organ segmentation, adapt the deep learning framework to be compatible with incomplete training data, improve the CNN models upon arrival of new training data, and post-process the output from the deep learning framework to obtain final organ segmentation.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Reference will now be made to the accompanying drawings, which are not necessarily drawn to scale.

DETAILED DESCRIPTION

Reference will now be made in detail to example embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the disclosure. Instead, they are merely examples of apparatuses and methods consistent with aspects related to the disclosure as recited in the appended claims.

The terminology used in the present disclosure is for the purpose of describing particular embodiments only and is not intended to limit the present disclosure. As used in the present disclosure and the appended claims, the singular forms "a," "an," and "the" are intended to include the plural forms as well, unless the context clearly indicates otherwise. It shall also be understood that the term "and/or" used herein is intended to signify and include any or all possible combinations of one or more of the associated listed items.

It shall be understood that, although the terms "first," "second," "third," etc. may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to a judgment" depending on the context.

The present disclosure related to a deep learning framework for automatic thoracic organ segmentation including spinal cord, left and right lungs, heart and esophagus. The disclosure is not limited to these five organs and can be easily extended to other organs.

Figure 1:
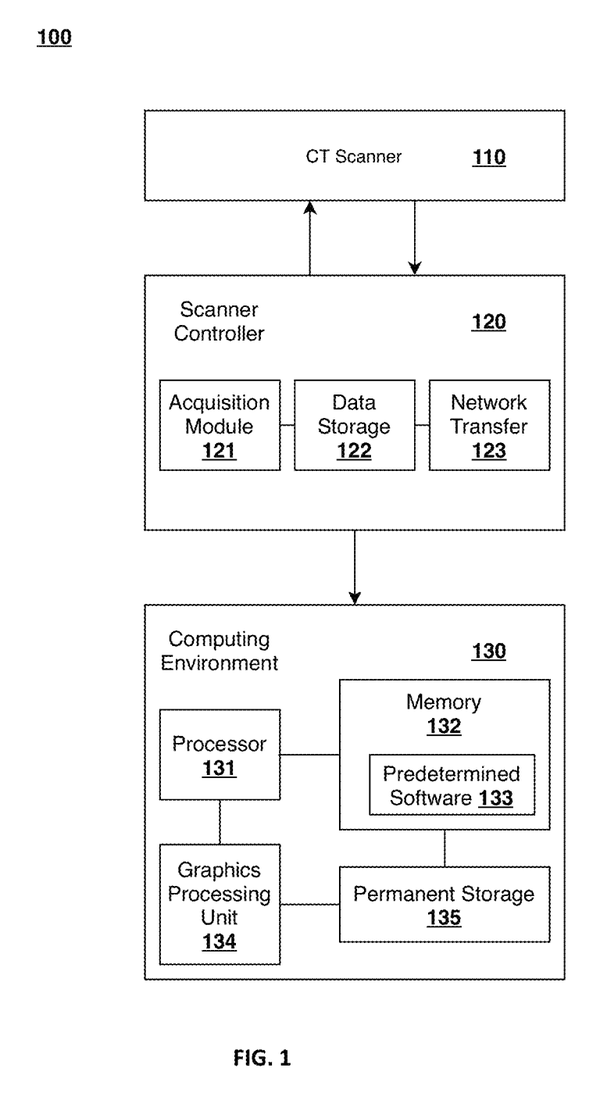
FIG. 1 is a system diagram of CT scanner, controller and computing environment illustrating an operating environment capable of implementing aspects of the present disclosure.

FIG. 1 shows a system diagram of CT scanner 110, controller 120 and computing environment 130. The CT scanner 110 is used to obtain CT images covering the thoracic region of a subject and is controlled by the scanner controller 120. The scanner controller 120 contains the acquisition module 121 that drives the CT scanner 110, the data storage module 122 that stores the CT images of different subjects, and the network transfer module 123 that sends the CT images to other computing environment 130. The computing environment 130 contains processor 131, graphics processing unit 134, memory 132 and permanent storage 135 to perform given directions. In executing the directions, the predetermined software 133 is loaded into memory 132 and executed by processor 131 to yield the desired output.

The processing component 120 typically controls overall operations of the computing environment 130, such as the operations associated with display, data acquisition, data communications, and image processing. The processor 131 may include one or more processors to execute instructions to perform all or some of the steps in the above described methods. Moreover, the processor 131 may include one or more modules which facilitate the interaction between the processor 131 and other components. The processor may be a Central Processing Unit (CPU), a microprocessor, a single chip machine, a GPU, or the like. GPU 134 can include one or more GPUs interconnected to execute one or more GPU executable programs.

The memory 132 is configured to store various types of data to support the operation of the computing environment 130. Examples of such data comprise instructions for any applications or methods operated on the computing environment 130, CT datasets, image data, etc. The memory 132 may be implemented by using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

In an embodiment, the computing environment 130 may be implemented with one or more application specific integrated circuits (ASICs), digital signal processors (DSPs), digital signal processing devices (DSPDs), programmable logic devices (PLDs), field programmable gate arrays (FPGAs), graphical processing units (GPUs), controllers, micro-controllers, microprocessors, or other electronic components, for performing the above methods.

The automatic thoracic organ segmentation method using a deep learning framework is programmed as one set of predetermined software 133 and installed on the computing environment 130. When the computing environment 130 receives CT images from scanner controller 120, the predetermined software 133 is executed to generate the segmentation results.

Figure 2:
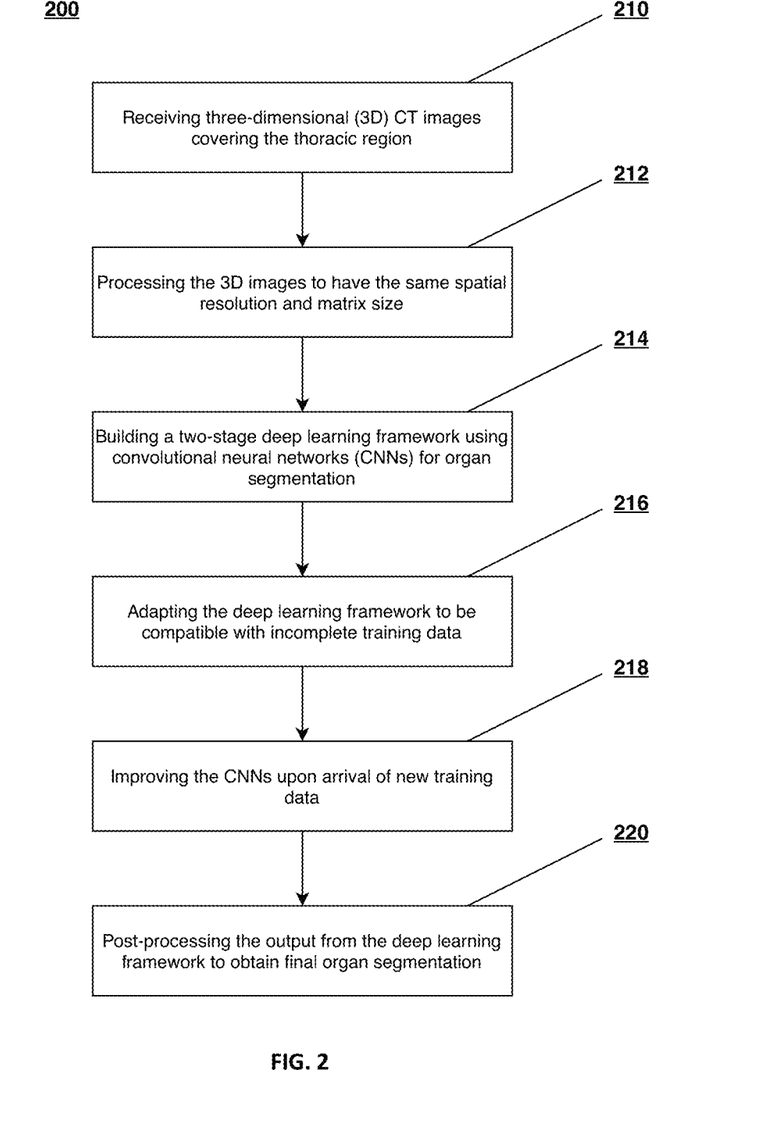
FIG. 2 is a flow chart illustrating a method for automatic thoracic organ segmentation using a deep learning framework, according to an example of the present disclosure.

FIG. 2 shows an example flow chart setting forth the steps of a method 200 in accordance with the present disclosure.

Figure 4:
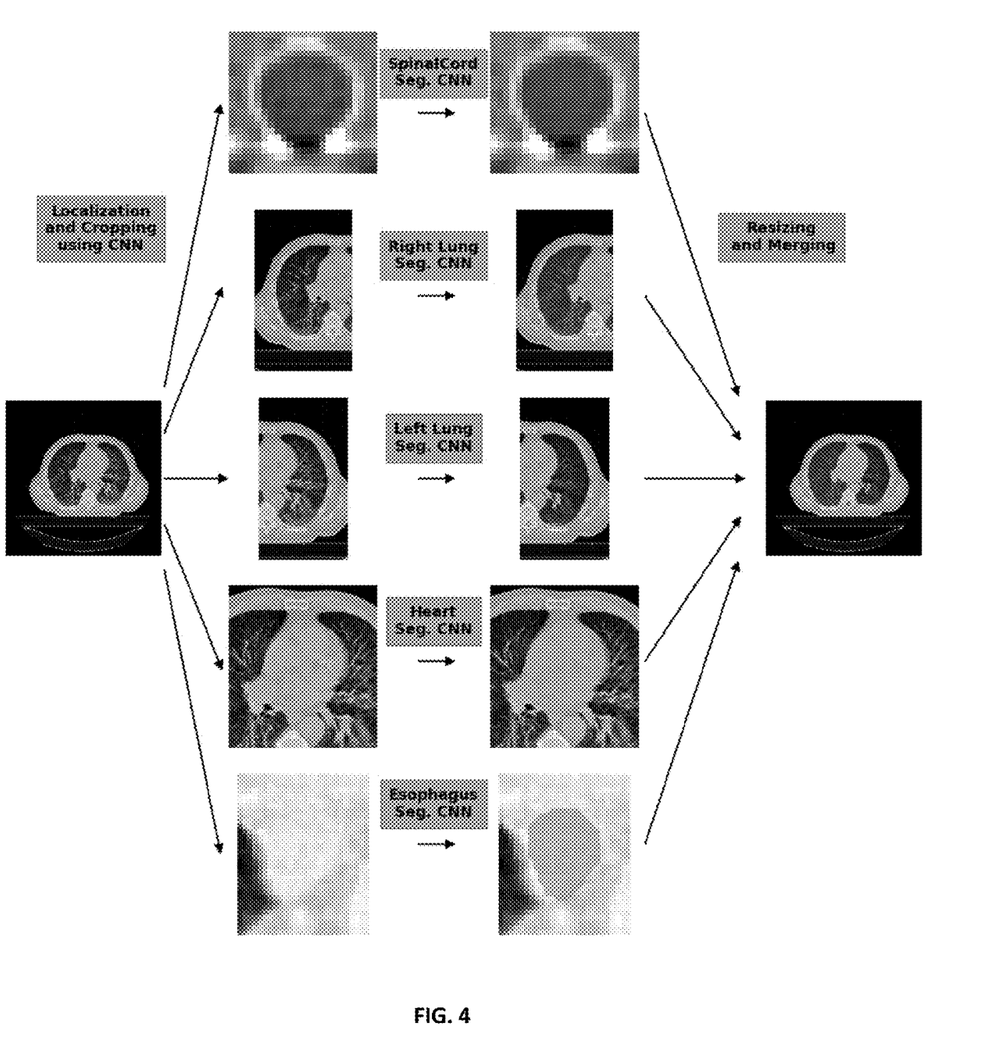
FIG. 4 is a workflow diagram illustrating the deep learning framework for thoracic organ segmentation, according to an example of the present disclosure.
Figure 5A:
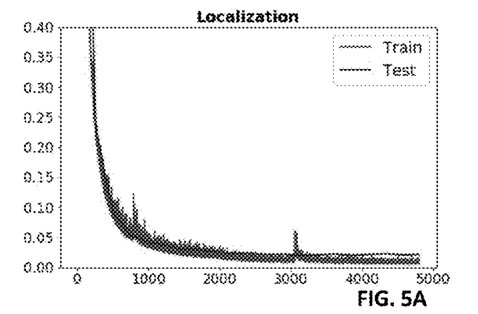
FIG. 5A is a loss curve for training and testing CT images during the CNN training process for the first stage network (Localization), according to an example of the present disclosure.
Figure 5B:
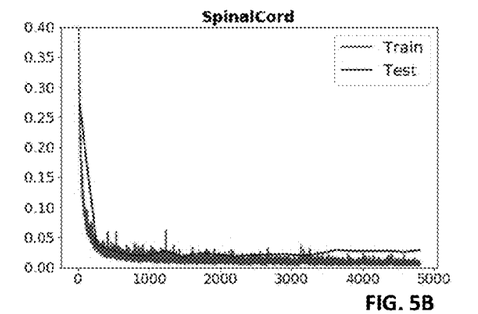
FIG. 5B is a loss curve for training and testing CT images during the CNN training process for the spinal cord (SpinalCord) of the second stage network, according to an example of the present disclosure.
Figure 5C:
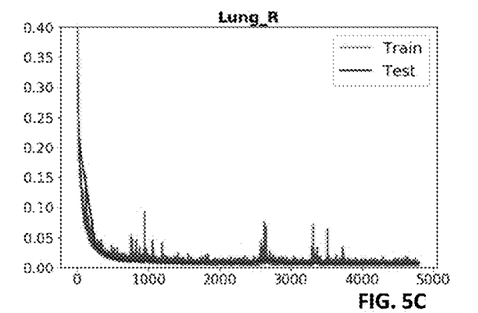
FIG. 5C is a loss curve for training and testing CT images during the CNN training process for the right lung (Lung_R) of the second stage network, according to an example of the present disclosure.
Figure 5D:
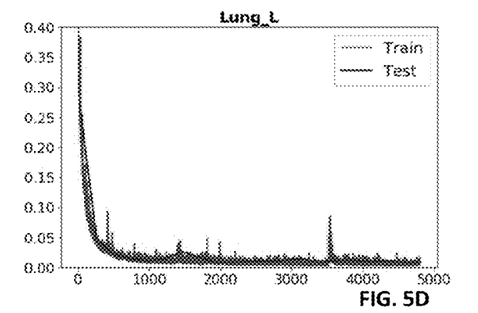
FIG. 5D is a loss curve for training and testing CT images during the CNN training process for the left lung (Lung_L) of the second stage network, according to an example of the present disclosure.
Figure 5E:
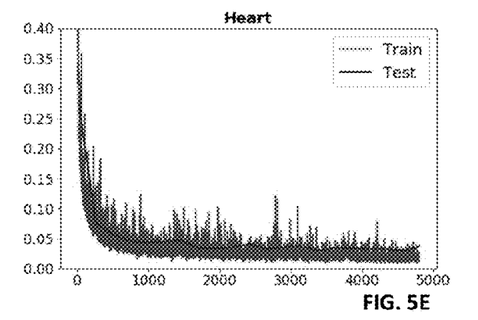
FIG. 5E is a loss curve for training and testing CT images during the CNN training process for the heart (Heart) of the second stage network, according to an example of the present disclosure.
Figure 5F:
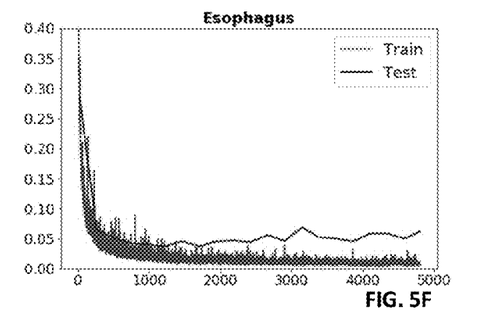
FIG. 5F is a loss curve for training and testing CT images during the CNN training process for the esophagus (Esophagus) of the second stage network, according to an example of the present disclosure.
Figure 6A:
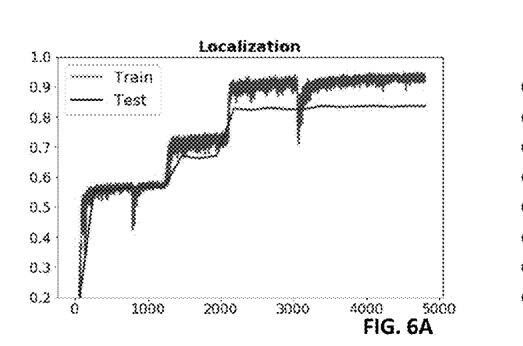
FIG. 6A is a Dice value curve for training and testing CT images during the CNN training process for the first stage network (Localization), according to an example of the present disclosure.
Figure 6B:
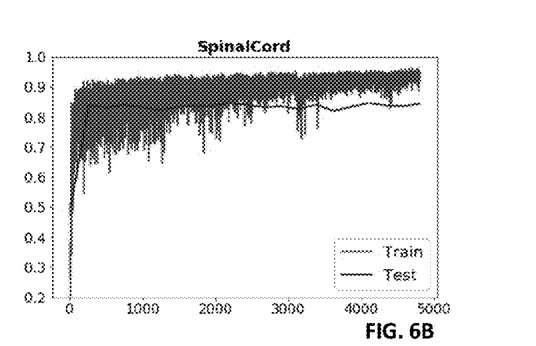
FIG. 6B is a Dice value curve for training and testing CT images during the CNN training process for the spinal cord (SpinalCord) of the second stage network, according to an example of the present disclosure.
Figure 6C:
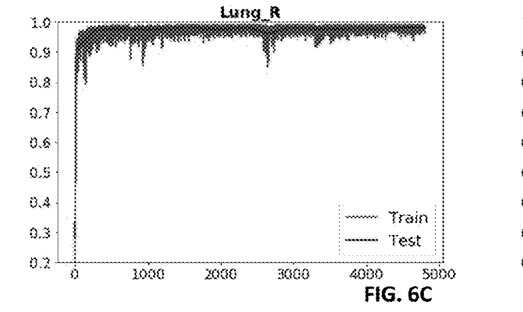
FIG. 6C is a Dice value curve for training and testing CT images during the CNN training process for the right lung (Lung_R) of the second stage network, according to an example of the present disclosure.
Figure 6D:
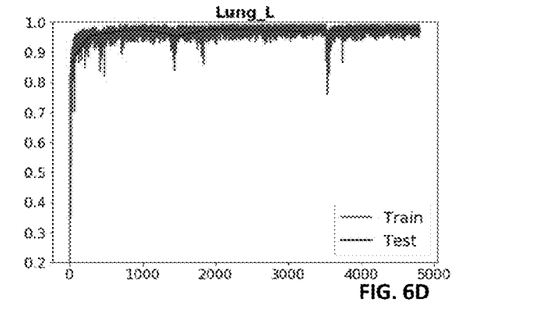
FIG. 6D is a Dice value curve for training and testing CT images during the CNN training process for the left lung (Lung_L) of the second stage network, according to an example of the present disclosure.
Figure 6E:
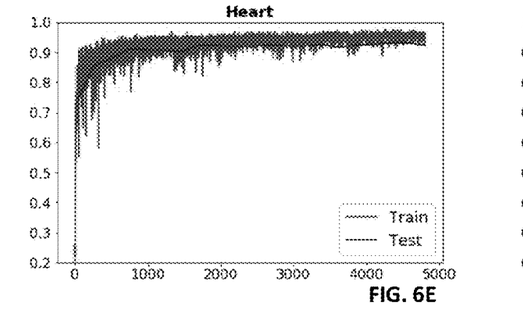
FIG. 6E is a Dice value curve for training and testing CT images during the CNN training process for the heart (Heart) of the second stage network, according to an example of the present disclosure.
Figure 6F:
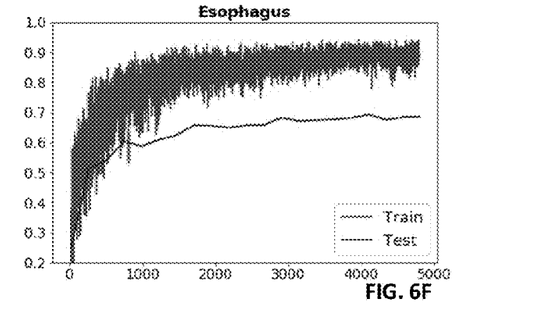
FIG. 6F is a Dice value curve for training and testing CT images during the CNN training process for the esophagus (Esophagus) of the second stage network, according to an example of the present disclosure.
Figure 7A:
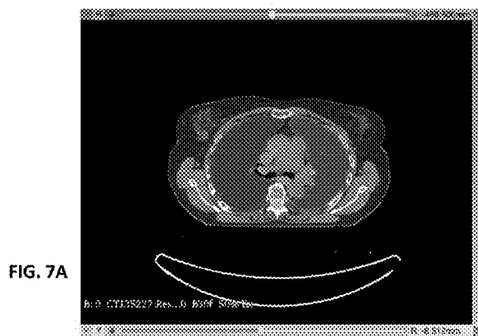
FIG. 7A is an axial slice illustrating the CT image and the organ segmentations, according to an example of the present disclosure.
Figure 7B:
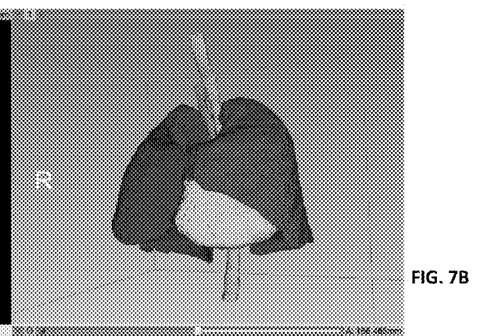
FIG. 7B is a 3D display of the organ segmentations, according to an example of the present disclosure.
Figure 7C:
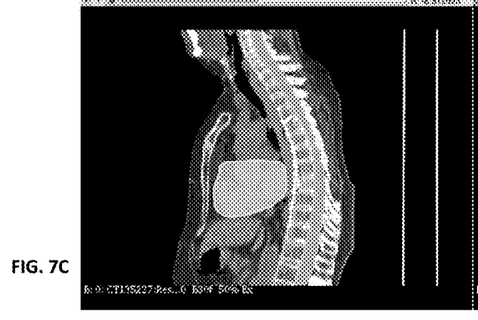
FIG. 7C is a sagittal slice illustrating the CT image and the organ segmentations, according to an example of the present disclosure.
Figure 7D:
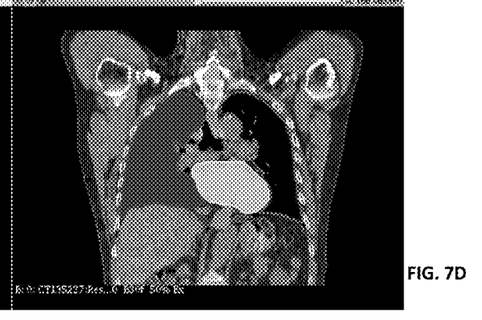
FIG. 7D is a coronal slice illustrating the CT image and the organ segmentations, according to an example of the present disclosure.

In step 210, three-dimensional (3D) CT images covering the thoracic region are received. For example, one axial slice of the 3D CT images is shown in FIG. 4.

In step 212, the 3D CT images are processed to have the same spatial resolution and matrix size.

As the CT imaging protocol including pixel spacing, axial slice thickness and field-of-view in the z-direction can vary from different scans, to reduce the variability within the dataset including both training and testing cases, the input images were all uniformly resampled to have axial in-plane resolution of $0.9756 \times 0.9756$ mm$^2$ and 3 mm slice-thickness. The in-plane matrix size was fixed to $512 \times 512$ so that the corresponding field-of-view was $500 \times 500$ mm$^2$. Each image dataset was either zero-padded or center-cropped in the axial plane after resampling. The resulting image matrix size was $512 \times 512 \times N$, in which N is the number of slices after resampling.

For training cases, of which the ground-truth contours were available, the corresponding label maps were generated using the same pre-processing pipeline with the values at each voxel indicating its region-of-interest (ROI) label. To normalize the image intensity, the voxel values outside of −1000 to 600 Hounsfield unit (HU) were set to −1000 and 600, respectively. Resulting images were then normalized to the range [0, 1].

Two datasets were used in this study: 2017 American Association of Physics in Medicine (AAPM) Thoracic Auto-segmentation Challenge and a private dataset from the University of Kentucky (UK). The challenge dataset contains 60 thoracic CT scans from three clinical sites (MD Anderson Cancer Center, Memorial Sloan-Kettering Cancer Center and MAASTRO clinic) with 20 cases from each institution. The datasets were divided into three groups with 36 training cases, 12 offline test cases, and 12 online test cases. The contours were manually drawn following the RTOG 1106 contouring guidelines and were quality checked. To be able to evaluate the automatic algorithms with respect to human performances, the inter-rater variability was obtained by three experts on three cases. The dataset from UK contains 30 randomly selected thoracic CT scans. IRB approval was obtained for retrospective clinical data usage for research. To reduce the time for manually segmenting the OARs, automatic segmentation was first performed using the proposed method trained on the challenge training dataset and the resulting contours were verified and edited as the final ground truth contours.

Pre-processing, while often overlooked, is a key step in the network performance. The most important step is assumed to be the intensity cropping and normalization. As there are often very bright regions from external objects in the images, they will have a large effect on the organ voxel values when normalizing using the original intensity range. Resampling the images to the same voxel spacing was assumed to help as well since it reduced the variability in the organ sizes measured in matrix size and brought the testing case distribution closer to the training case distribution.

In step 214, a two-stage deep learning framework using convolutional neural networks (CNNs) is built for organ segmentation.

Figure 3:
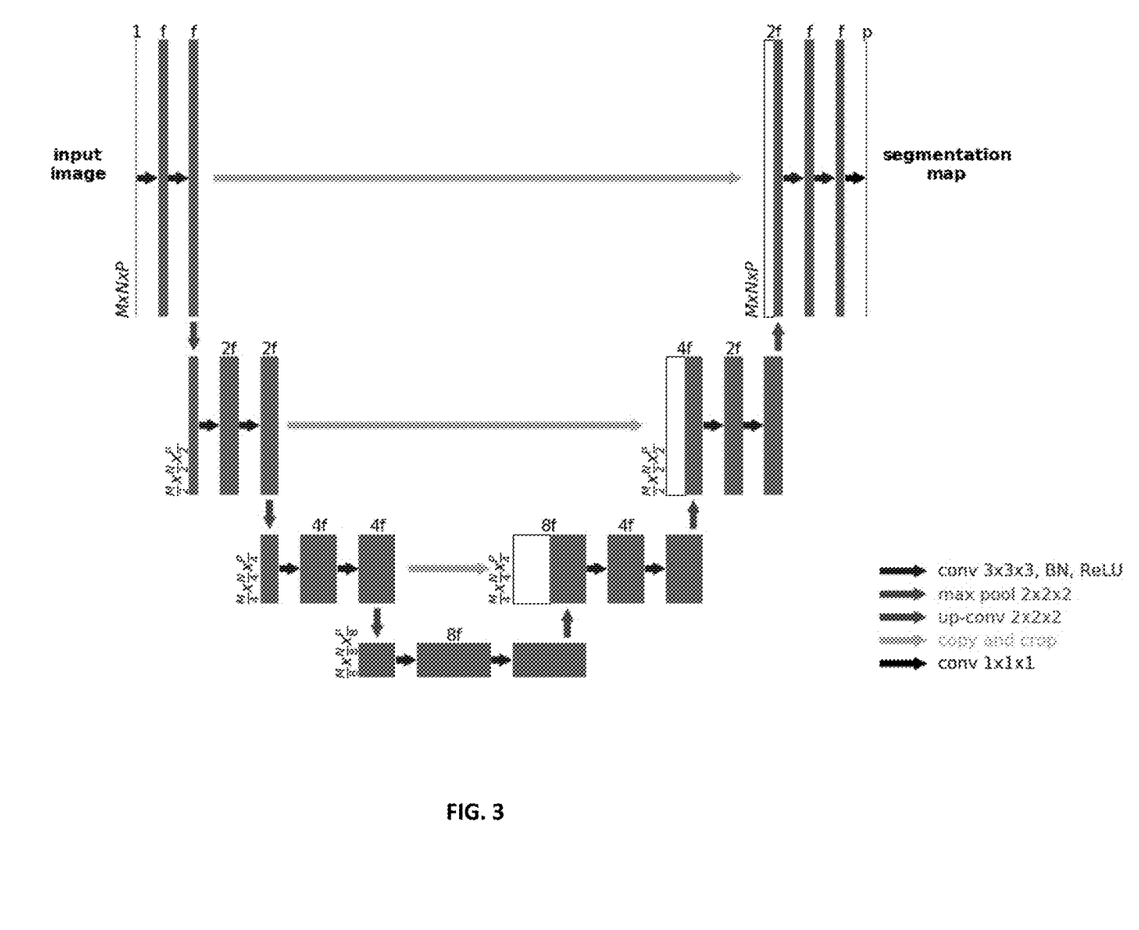
FIG. 3 is a convolutional neural network structure, according to an example of the present disclosure.

FIG. 3 shows a CNN structure denoted as the 3D U-Net. General structure for 3D U-Net used in this application. Each encoding block consists of two sets of consecutive convolutions, batch norm and rectifier linear activation layers. Padding was used to maintain the spatial dimension during convolution. Number of features were doubled after each pooling layer. Long range connections were used by concatenating the outputs from the corresponding encoding blocks with the decoding blocks. M, N, P, f and p are parameters that are unique for each network.

The input images are first re-sampled and then center-cropped to M×N×P and the number of features is set to be smaller than was used in the original U-Net. M is the image size along the superior-inferior direction, N is along the anterior-posterior direction and P is along the left-right direction. Two sets of 3D convolution filters of $3 \times 3 \times 3$, batch normalization layer and the rectified linear activation function are used for each encoding block. Padding is used for each convolution operation to maintain the spatial dimension. With each pooling step, the spatial dimension is reduced in all directions and the number of features is doubled. The final segmentation map contained 6 classes: background and one for each organ.

The 3D U-Net architecture can fully exploit the volumetric spatial information and thus is a preferred choice for 3D organ segmentation. It is often trained end-to-end from input images and the corresponding labels with the same size. However, using the entire 3D thoracic CT images as the input is limited by the GPU memory and is suboptimal in terms of training time and accuracy as there are a large number of irrelevant voxels for segmentation of a specific organ, which may also lead to an increase in the number of false positives. Considering that each organ to be segmented has a relatively fixed location within thoracic CT images, a three-step segmentation modeling is developed: first, the organs to be segmented are localized and the original 3D thoracic images are separately cropped to patches of a much smaller sizes with each patch containing only one organ; second, individual models are trained to segment the organ from the cropped images; finally, the segmentation results for each organ are resampled to the original image size and merged together to obtain the final label map.

FIG. 4 shows the workflow on a sample 2D slice using the aforementioned framework. The 3D thoracic images were first cropped to smaller patches containing only one organ. Individual CNN models were then used to segment the organ for each cropped patch. The resulting segmentations were resampled and merged to get the final multi-organ label map.

Detection networks, which output the center and dimension of regional bounding boxes, are considered for the initial organ localization step. However, such networks are difficult to train using small datasets. Instead, as the ground truth label map is available, a multi-label segmentation network based on a 3D U-Net is used for this step as they are relatively easier to train since the regional information is provided on the voxel level. The bounding boxes for each organ can then be easily extracted from the predicted label maps. As claimed previously, the input images need to be substantially under-sampled and a simpler network needs to be used for the model to fit into GPU memory. Although the segmentation quality is sub-optimal, it is assumed to provide sufficient information for relatively accurate localization. Furthermore, additional steps during cropping and training of the second-stage segmentation networks are performed to improve the model robustness against inaccuracy in localization, which will be addressed later in this sub-section.

During training, data augmentation is performed by applying random translations, rotations and scaling to the input images and the corresponding ground-truth label maps at each iteration. After applying the random transformations to the label maps, a threshold value of 0.5 is applied to each interpolated organ segmentation to convert back to binary values.

With the label maps of each organ, which are provided as the ground truth for training data set and obtained from the localization network for testing data set, cropping can be performed separately on the original 3D images to get the input of each segmentation network. For simplicity, the voxels inside the organ are denoted as foreground and outside the organ are denoted as background voxels. Although the foreground voxels are assumed to play dominant role for accurate segmentation, inclusion of background voxels close to the boundary can provide additional information for the segmentation network to learn. Therefore, during cropping, after the exact range of the organ is obtained, a bounding box slightly larger than the range will be used for cropping. Specifically, the following equations were used to determine the starting and ending coordinates:

$$i_{start} = \text{Max}(0, i_{min} - \alpha^*(i_{max} - i_{min}))$$

$$i_{end} = \text{Min}(D_i, i_{max} + \beta^*(i_{max} - i_{min}))$$

in which $i_{max}$ and $i_{min}$ are the maximum and minimal coordinates of all foreground voxels along axis i, $D_i$ is the corresponding image size along dimension i, and $\alpha$ and $\beta$ are scalar values within a given range.

During the training phase of each segmentation network, $i_{max}$ and $i_{min}$ are obtained from the ground truth label maps, $\alpha$ and $\beta$ are randomly generated between 0.1 and 0.7 using a uniform distribution for all three axes and during every iteration as a data augmentation mechanism to accommodate for inaccuracy in boundary determination when the ground truth label map is unavailable. During the testing phase, $i_{max}$ and $i_{min}$ are obtained from the output label map of the localization network after padding and resizing to the original dimension. To further increase the performance of the segmentation network, multiple values of $\alpha$ and $\beta$ are used to get slightly different cropped images and each one was feed into the segmentation network to get the corresponding output result. The multiple outputs are then averaged after resizing to the original dimension to get the final segmentation results. Although using a larger number of cropped images would be expected to improve the results, the computation time would also be greatly increased and the improvement tends to diminish when the number is already large. In practice, 6 sets of cropped images are used for each organ. To make the segmentation results consistent over different experiments, the random values of $\alpha$ and $\beta$ are pre-generated in the beginning and fixed for all testing runs.

For each organ, a 3D U-Net with the same network structure shown in FIG. 3 is used for foreground and background segmentation. The cropped images are resampled to a fixed input size, which is determined from the average cropped sizes. The numbers of filters are larger than the localization network to increase the complexity and expressiveness of the network. Although the imbalance of the foreground and background voxels is reduced with the cropped images, the weighted cross-entropy loss is still used for smaller organs to increase the sensitivity. For the spinal cord, the weights are 2.0 and 1.0 for foreground and background, respectively. For the esophagus, the weights are 3.0 and 1.0. The Adam optimizer with learning rate 0.0005 is used and the training process is run for 200 epochs. Additional parameters are provided in Table 1.

Table 1 shows the network parameters for the localization network and the organ specific networks.

TABLE 1

3D U-Net parameters for localization and segmentation of each organ (M, N, P are the spatial dimensions, f is the number of filters in the first encoding block, p is the number of output labels)

|  | M | N | P | f | P |
| --- | --- | --- | --- | --- | --- |
| Localization | 72 | 208 | 208 | 24 | 6 |
| SpinalCord | 160 | 128 | 64 | 64 | 2 |
| Lung_R | 72 | 192 | 120 | 48 | 2 |
| Lung_L | 72 | 192 | 120 | 48 | 2 |
| Heart | 32 | 160 | 192 | 64 | 2 |
| Esophagus | 80 | 80 | 64 | 64 | 2 |

During training, data augmentation is first performed during the cropping stage, as described before. Additional random rotation and shear transformations are then applied to the input after resampling the cropped images. During testing, augmentation using different cropped images is performed. The output probability image corresponding to the foreground class, obtained as the output of the final soft-max layer in the network, is resized to the cropped images and zero-padded to the original dimension for each input. The final results are averaged probability maps of each voxel belonging to one organ. Due to cropping, the probability of the voxels outside of the cropped regions is 0.

FIG. 5 shows the weighted cross-entropy loss of the training cases and testing cases during training for the localization network (FIG. 5A) and five organ segmentation networks (FIG. 5B, 5C, 5D, 5E, 5F). Training and testing converge very fast for the organ segmentation networks due to the relatively easy task of binary segmentation. Testing loss follows the same trend with training loss and has similar values except for the spinal cord and esophagus, which slightly increases towards the end of the training process, indicating minor overfitting.

FIG. 6 shows the Dice scores of the training cases and testing cases during training for the localization network (FIG. 6A) and five organ segmentation networks (FIG. 6B, 6C, 6D, 6E, 6F). The Dice scores of the localization network shows step-wise increase, meaning that the segmentation of different organs is learned consecutively rather than simultaneously. Spinal cord and esophagus have much lower Dice scores for the testing cases than training cases. Although the loss slightly increases for these two organs, the testing Dice scores are stable or slowly increasing.

For further evaluation, when ground-truth contours are available, the automatic segmentation results can be evaluated using the Dice coefficient, mean surface distance and 95% Hausdorff distance. The Dice coefficient (D) is calculated as:

$$D = \frac{2|X \cap Y|}{|X|+|Y|}$$

where X and Y are the ground truth and the algorithm segmented contours, respectively. The directed average Hausdorff measure is the average distance of a point in X to its closest point in Y, given as $$\vec{d}_{H,avg}(X, Y) = \frac{1}{|X|} \sum_{x \in |X|} \min_{y \in |Y|} d(x, y)$$

The mean surface distance (MSD) is then defined as the average of the two directed average Hausdorff measures:

$$MSD = \frac{\vec{d}_{H,avg}(X, Y) + \vec{d}_{H,avg}(Y, X)}{2}$$

The 95% directed percent Hausdorff measure is the $95^{th}$ percentile distance over all distances from points in X to their closest point in Y. Demoting the $95^{th}$ percentile as $K_{95}$, this is given as:

$$\vec{d}_{H,95}(X,Y) = K_{95}(\min_{y \in |Y|} d(x,y)) \forall x \in X$$

The undirected 95% Hausdorff distance (HD95) is then defined as the average of the two directed distances:

$$HD95 = \frac{\vec{d}_{H,95}(X, Y) + \vec{d}_{H,95}(Y, X)}{2}$$

Table 2 shows the performances evaluated by Dice, MSD and HD95 on a separate testing dataset.

TABLE 2

Dice scores, MSD and HD of the testing dataset

|  | Dice | MSD (mm) | HD95 (mm) |
|---|---|---|---|
| SpinalCord | 0.893 ± 0.044 | 0.662 ± 0.248 | 1.893 ± 0.627 |
| Lung_R | 0.972 ± 0.021 | 0.933 ± 0.574 | 3.958 ± 2.845 |
| Lung_L | 0.979 ± 0.008 | 0.586 ± 0.285 | 2.103 ± 0.938 |
| Heart | 0.925 ± 0.015 | 2.297 ± 0.492 | 6.570 ± 1.501 |
| Esophagus | 0.726 ± 0.094 | 2.341 ± 2.380 | 8.714 ± 10.588 |

FIG. 7 shows automatically segmented 5 organs on a test case using the proposed framework. FIGS. 7A, 7C, and 7D show the axial, sagittal and coronal slices, respectively. FIG. 7B shows the 3D view of the segmentations. All organs have satisfactory contours with no obvious mistakes. Minimal human interaction is needed.

One challenge in deep learning framework is the reliance on training data. In practice, two issues can exist for a training dataset: incomplete labeling and systemic differences.

For example, in thoracic organ segmentation, each training data contains the CT images and the ground truth contours for the organs. However, it is possible that some of the training data do not contain the contours for all organs, but instead missing spinal cord or esophagus. In this case, the two-stage deep learning framework needs to be adapted to be compatible with incomplete training data.

In step 216, the deep learning framework is adapted to handle incomplete training data.

One solution to handle incomplete training data is to simply throw away data with incomplete labeling; however, it is a waste of resources as these data contain useful information. The following method is developed to take the most advantage of all available data.

During training, ambiguity is introduced in the loss function to avoid punishing the missing organs. More specifically, with cross-entropy loss function (CE), only voxels from labeled organs are counted; with Dice loss function (D), the Dice is ignored for missing organs. The following equations give the corresponding loss functions when there are no missing organs, i.e., contours for all five organs exist:

$$CE = -\sum_{c=1}^{6} y_{o,c} \log(p_{o,c})$$

$$D = 1 - \frac{1}{5} * \sum_{c=1}^{5} d_c$$

$$d_c = 2.0 * \text{intersection/union}$$

in which $y_{o,c}=1$ for correct label for voxel o. When there are missing organs, CE is modified to have $y_{o,c}=0$ for all c to ignore all background voxels and the missing organs are ignored; D is modified to ignore the missing organs as well.

Due to different CT scanners and different acquisition protocol in different clinical sites, the CT images may contain systematic differences, causing the model trained using the data from one clinical site to perform much worse in another site. This is a common issue in deep learning frameworks. However, in practice, it is difficult to collect data from different sites at once before training CNNs.

In step 218, the CNNs are improved upon arrival of new data to address the issue of systematic differences of the CT images and the fact that they can arrive at different times.

Figure 8A:
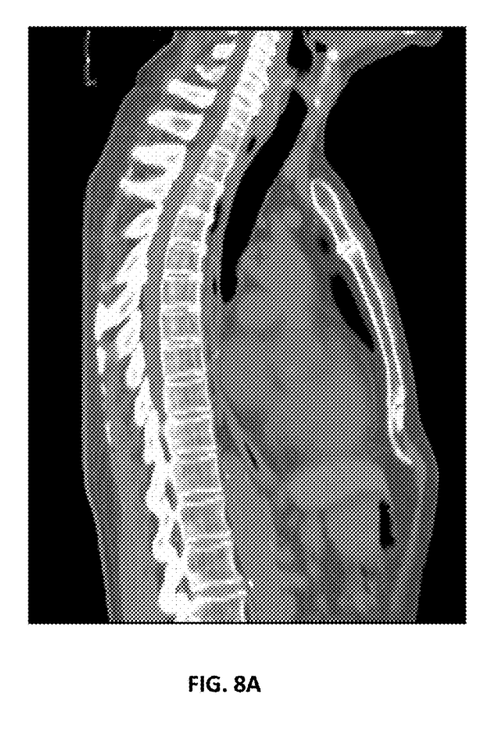
FIG. 8A is a sagittal slice illustrating the CT image and the heart segmentation from one patient without using belly compression, according to an example of the present disclosure.
Figure 8B:
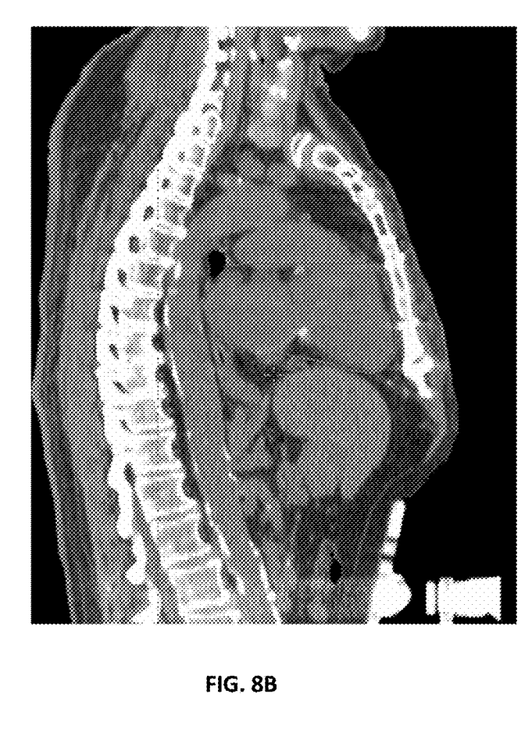
FIG. 8B is a sagittal slice illustrating the CT image and the heart segmentation from one patient using belly compression, according to an example of the present disclosure.

FIG. 8 shows an example case from two institutions. Belly compression is a technique to suppress respiratory motion during CT image acquisition. However, it is not used in every clinical site due to various reasons. FIG. 8A shows one case acquired without using belly compression and FIG. 8B shows one case acquired using belly compression at a different site. The location of the heart shows systematic differences of the CT images.

The systematic differences cause the thoracic organ segmentation CNN model trained using one dataset (AAPM) to perform substantially worse on another dataset (University of Kentucky). In particular, heart segmentation completely fails as it extended to the abdomen in many cases. One possible reason for the discrepancy in performance is the subtle differences in CT appearance compared between the local and the challenge dataset. Although the most effective solution for this issue is to add more cases to the training set, the impact of the number of cases and the selection criteria is not well studied. Furthermore, transfer learning, in which the part or even the whole DCNN can be initialized from another network to reduce the training effort and/or improve the performance, has not been studied in such a scenario.

The University of Kentucky (UK) dataset contains 45 randomly selected thoracic CT scans. The institutional review board (IRB) approval is obtained for retrospective clinical data usage for research. Abdominal compression technique is used for motion management on most patients. CTs are acquired with a GE Lightspeed-16 scanner at 120 kVp. Clinically accepted contours are quality checked to ensure the adherence to the Radiation Therapy Oncology Group (RTOG) 1106 contouring guidelines, as followed by the challenge dataset. The UK dataset is further divided into 30 cases for enhancing the network performance with re-training and 15 for final evaluation.

To update the model with new cases, the same procedure is followed as in the original framework. The model is first re-trained from scratch with a learning rate of 0.0005 and epochs of 200 for both the localizer and organ specific segmentation networks. Alternatively, for the transfer learning experiment, the network weights from the original model are first loaded and fine-tuned using the new dataset. As all layers may contribute to the segmentation accuracy, no layer is "frozen" during the fine-tuning process; instead, the same loss is back-propagated to each layer. As the Adam optimizer used in the training process can automatically adapt the learning rate, the same learning rate of 0.0005 is used; however, the number of epochs is reduced to 100 as the network is initialized with meaning parameters. To reduce overfitting, random 3D translation, rotation and scaling are applied to the input images and the corresponding ground-truth label maps as data augmentation. First, all 30 UK training cases are mixed with the challenge data to train a model from scratch and with transfer learning from the original model, respectively. The original model is deployed on the 30 UK training cases, which are then ranked based on the overall segmentation accuracy.

Figure 9A:
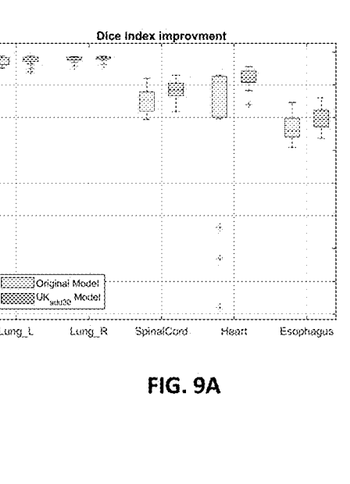
FIG. 9A is Dice score chart before and after CNN model improvement with new data, according to an example of the present disclosure.
Figure 9B:
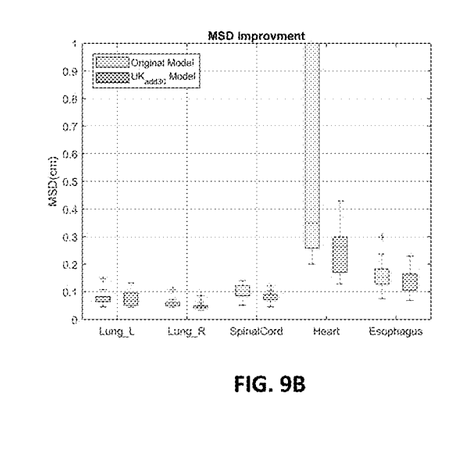
FIG. 9B is mean surface distance (MSD) chart before and after CNN model improvement with new data, according to an example of the present disclosure.
Figure 9C:
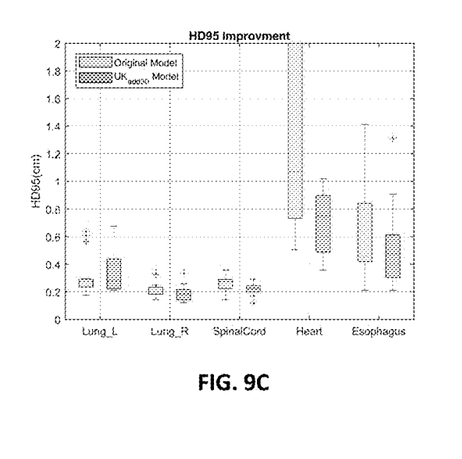
FIG. 9C is 95 Hausdorff distance (HD95) chart before and after CNN model improvement with new data, according to an example of the present disclosure.
Figure 10A:
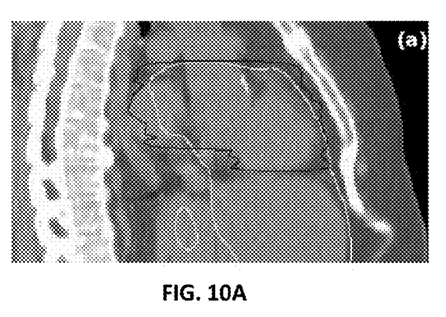
FIG. 10A is a sagittal slice illustrating the CT image and the heart segmentation before CNN model improvement, according to an example of the present disclosure.
Figure 10B:
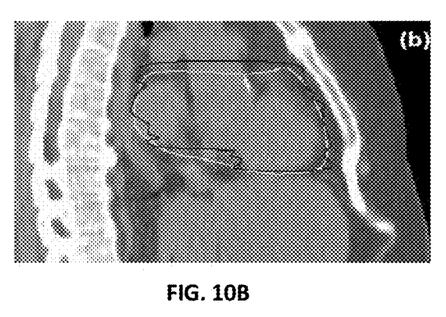
FIG. 10B is a sagittal slice illustrating the CT image and the heart segmentation after CNN model improvement, according to an example of the present disclosure.
Figure 10C:
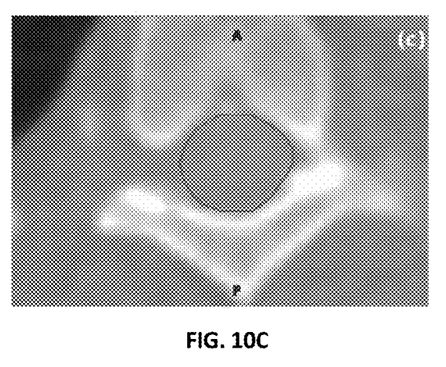
FIG. 10C is an axial slice illustrating the CT image and the spinal cord segmentation before CNN model improvement, according to an example of the present disclosure.
Figure 10D:
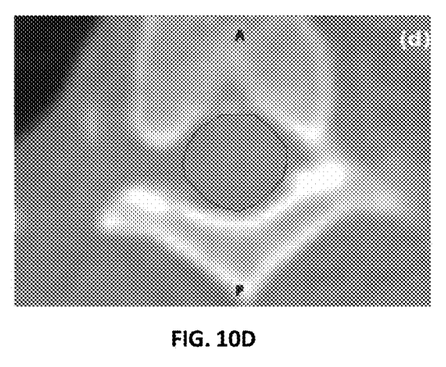
FIG. 10D is an axial slice illustrating the CT image and the spinal cord segmentation after CNN model improvement, according to an example of the present disclosure.

FIG. 9 shows the DSC (FIG. 9A), MSD (FIG. 9B) and HD95 (FIG. 9C) achieved on the 15 UK test dataset using the original model (UKorig) and the model trained from scratch with 30 UK cases added to the original challenge training dataset (UKadd30).

For a better comparison against the performances achieved in the challenge testing dataset and the inter-observer variability from the experiment conducted by the challenge organizers, the mean and standard deviation of DSC, MSD and HD95 are listed in Table 3, 4 and 5, respectively. The metrics that are better than human expert's contouring variability are highlighted in bold.

TABLE 3

DSC achieved by the original model (UKorig) and improved model by adding 30 UK cases and trained from scratch and using transfer learning. The inter-observer value and evaluated on the challenge test cases were also shown as a comparison. Values in Bold indicates better than expert contouring variability.

| | Inter observer | Challenge | UKorig | UKadd30 (scratch) | UKadd30 (transfer) |
|---|---|---|---|---|---|
| SpinalCord | 0.862 | 0.89 ± 0.04 | 0.85 ± 0.04 | 0.88 ± 0.03 | 0.89 ± 0.02 |
| Lung_R | 0.955 | 0.97 ± 0.02 | 0.97 ± 0.01 | 0.98 ± 0.01 | 0.98 ± 0.01 |
| Lun _L | 0.956 | 0.98 ± 0.01 | 0.98 ± 0.01 | 0.98 ± 0.01 | 0.98 ± 0.01 |
| Heart | 0.931 | 0.93 ± 0.02 | 0.79 ± 0.23 | 0.92 ± 0.03 | 0.91 ± 0.09 |
| Esophagus | 0.818 | 0.73 ± 0.09 | 0.77 ± 0.04 | 0.80 ± 0.04 | 0.78 ± 0.04 |

TABLE 4

MSD in mm achieved by the original model (UKorig) and improved model by adding 30 UK cases and trained from scratch and using transfer learning. The inter-observer value and evaluated on the challenge test cases were also shownas a comparison. Values in Bold indicates better than expert contouring variability.

| | Inter observer | Challenge | UKorig | UKadd30 (scratch) | UKadd30 (transfer) |
|---|---|---|---|---|---|
| SpinalCord | 0.88 | 0.7 ± 0.3 | 1.0 ± 0.3 | 0.8 ± 0.2 | 0.7 ± 0.1 |
| Lung_R | 1.87 | 0.9 ± 0.6 | 0.8 ± 0.3 | 0.7 ± 0.3 | 0.7 ± 0.2 |
| Lung_L | 1.51 | 0.6 ± 0.3 | 0.6 ± 0.2 | 0.5 ± 0.1 | 0.5 ± 0.1 |
| Heart | 2.21 | 2.3 ± 0.5 | 9.5 ± 11.8 | 2.5 ± 0.8 | 3.0 ± 1.7 |
| Esophagus | 1.07 | 2.3 ± 2.4 | 1.6 ± 0.5 | 1.4 ± 0.4 | 1.5 ± 0.4 |

TABLE 5

HD95 in mm achieved by the original model (UKorig) and improved model by adding 30 UK cases and trained from scratch and using transfer learning. The inter-observer value and evaluated on the challenge test cases were also shown as a comparison. Values in Bold indicates better than expert contouring variability.

| | Inter observer | Challenge | UKorig | UKadd30 (scratch) | UKadd30 (transfer) |
|---|---|---|---|---|---|
| SpinalCord | 2.38 | 1.9 ± 0.6 | 2.5 ± 0.6 | 2.2 ± 0.4 | 2.1 ± 0.3 |
| Lung_R | 6.71 | 4.0 ± 2.9 | 3.2 ± 1.5 | 3.5 ± 1.6 | 2.9 ± 1.3 |
| Lung_L | 5.17 | 2.1 ± 0.9 | 2.2 ± 0.5 | 1.8 ± 0.6 | 1.9 ± 0.6 |
| Heart | 6.42 | 6.6 ± 1.5 | 26.7 ± 28.8 | 7.1 ± 2.2 | 10.0 ± 8.1 |
| Esophagus | 3.33 | 8.7 ± 11 | 6.2 ± 3.4 | 5.2 ± 3.0 | 5.3 ± 2.4 |

When the original model is directly applied to UK data, a large drop in contouring accuracy is observed in heart. As shown in FIG. 9A, while the median DSC is still greater than 0.9, the distribution is heavily tilted to lower scores, with a few cases showing almost completely failed segmentation (DSC<0.5). The top quantile for HD95 and MSD for heart are much worse as well. Spinal cord contouring accuracy also decreased slightly. The esophagus shows a slightly better performance compared with the challenge, which is likely due to that the esophagus in the UK data is slightly easier to segment. After the model trained with the inclusion of UK data, the performance is significantly improved. The performances in heart and spinal cord increase to similar levels achieved in challenge. Esophagus performance also increase. Overall, 3 of the 5 organs segmented have performances significantly better than human expert's contouring variability and the remaining 2 organs achieve performances comparable with expert's contour variability.

The tables also show the comparison between training using transfer learning and from scratch. The overall performance is similar; however, for heart segmentation, although the mean DSC values are comparable, there are two cases with suboptimal performances, causing a substantial increase in its standard deviation and the two distance measures. This indicates that although transfer learning can significantly reduce the training time, it is not as effective as training from scratch in terms of "forgetting" the previous model as the failure mode in these two cases with transfer learning is similar as the previous model.

FIG. 10 shows examples of heart and spinal cord segmentation before and after the inclusion of local data in training. Green curves are ground truth segmentation. Magenta curves are auto-segmentation results. The re-training is performed from scratch. As in FIG. 10A, the main issue associated with heart is gross mis-segmentation that included part of liver with the original model. This problem is fixed after inclusion of local data in training (FIG. 10B). For spinal cord, the segmentation with original model is clinically acceptable as shown in FIG. 10C. However, due to the different contouring criteria used in the local ground truth, contouring evaluation metrics shows a slightly poorer score. At our institution, the dosimetrist prefers to contour spinal cord using a circular paintbrush sized appropriately to fit inside the spinal canal. Expansions from the circle are used conservatively. After the inclusion of local data in training, the model learnt this practice and produced segmentation that agrees with local ground truth better as illustrated in FIG. 10d.

The auto segmented contours are then evaluated by an expert physician. The review and editing time taken to produce clinical accepted contours is recorded. The contours from the original model require 7.5±3.8 mins for each case. After adding 30 local cases for re-training from scratch, the review and edit time for each case is reduced to 2.7±1.0 mins.

In the final step 220, since there may be overlaps in the cropped images for multiple organs, such as lung and heart, it is possible that the same voxel had a probability larger than 0.5 from multiple organ segmentation networks, meaning it would be classified as the foreground of multiple organs. To resolve such conflicts, the label for a particular voxel is chosen based on the maximum probability value greater than 0.5. Similar to the final post-processing step of the localization network, a single connected region is retained for each organ. Finally, the label maps are resampled to the same dimension as the original input before pre-processing and the corresponding contours are automatically calculated using the marching squares algorithm on each axial slice to get the segmentation results in DICOM-RT format.

In theory, post-processing is unnecessary since the CNN is expected to utilize all necessary information to get the best possible results and any post-processing algorithm should be part of the learning in a complex neural network. However, the current design of CNN cannot impose certain restrictions to the output, at least explicitly, such as the fact that all organs should be 3D-connected, smooth and conform to a certain shape. It is worth exploring how different constraints can be incorporated in the network structure itself. For post-processing, one issue is overfitting as any rule-based post-processing method may not apply to all cases. In this study, we do a simple 3D-connection analysis to remove small isolated regions, which is shown to be helpful in most cases, especially for the localization network. Other methods, such as Gaussian smoothing, help on certain failed cases. Further post-processing may depend on the probability output of the network, which can also be used to predict the reliability of the network without ground truth so that the application of post-processing can be case specific.

The proposed workflow also has its limitations. One major problem is the completely failed localization network, which cannot predict any labels for a certain OAR. In this case the cropping will be performed randomly and often cannot yield meaning results for the organ segmentation network. This was actually observed in one case during validation and caused 0 Dice score for esophagus. One possible solution is to use additional post-processing to detect it and rely on other information to crop the original images, such as the bounding boxes of other OARs. Further investigation will be performed to improve the robustness of the proposed method.

The proposed deep learning framework achieves good performance in the 2017 AAPM Thoracic Auto-segmentation Challenge by ranking 2nd in the live phase and ranking 1st with a later developed testing augmentation strategy.

What is claimed is:

1. A computer-implemented method for automatic thoracic organ segmentation using one or more processors, the method comprising:
    receiving three-dimensional (3D) images obtained by a computed tomography (CT) system;
    processing the 3D images to have the same spatial resolution and matrix size; building a two-stage deep learning framework using convolutional neural networks (CNNs) for organ segmentation;
    adapting the deep learning framework to be compatible with incomplete training data; improving the CNNs upon arrival of new training data;
    post-processing the output from the deep learning framework to obtain final organ segmentation;
    receiving 3D images and their corresponding information such as pixel spacing, slice thickness and matrix size;
    resizing the 3D images to have the same pixel spacing, matrix size; and
    applying lower and upper thresholds on the image intensities.

2. The computer-implemented method for automatic thoracic organ segmentation according to claim 1, building the two-stage deep learning framework comprises:
    training a localization CNN with the low-resolution CT images as the input and obtaining the locations of each organ.

3. The computer-implemented method for automatic thoracic organ segmentation according to claim 1, building the two-stage deep learning framework comprises:
    cropping the CT images based on the localization CNN output and using the cropped images as the input for organ specific CNN.

4. The computer-implemented method for automatic thoracic organ segmentation according to claim 1, adapting the deep learning framework to be compatible with incomplete training data comprises:
    using a modified cross entropy loss function and a modified Dice loss function to adapt the deep learning framework with incomplete training data.

5. The computer-implemented method for automatic thoracic organ segmentation according to claim 1, improving the CNNs upon arrival of new training data comprises:
    merging the new data with the old training data and using a transfer learning approach to update the CNNs.

6. The computer-implemented method or automatic thoracic organ segmentation according to claim 1, post-processing the output from the deep learning framework to obtain final organ segmentation comprises:

merging the output from different organ specific CNNs and resolving the conflicts based on the probabilities.

7. An apparatus for automatic thoracic organ segmentation, comprising:
one or more processors;
a display; and
a non-transitory computer readable memory storing instructions executable by the one or more processors, wherein the instructions are configured to:
receive three-dimensional (3D) images obtained by a computed tomography (CT) system;
process the 3D images to have the same spatial resolution and matrix size;
build a two-stage deep learning framework using convolutional neural networks (CNNs) for organ segmentation;
adapt the deep learning framework to be compatible with incomplete training data;
improve the CNNs upon arrival of new training data;
post-process the output from the deep learning framework to obtain final organ segmentation; and
display the organ segmentations;
receive 3D images and their corresponding information such as pixel spacing, slice thickness and matrix size;
resize the 3D images to have the same pixel spacing, matrix size; and
apply lower and upper thresholds on the image intensities.

8. The apparatus for automatic thoracic organ segmentation according to claim 7, building the two-stage deep learning framework comprises:
training a localization CNN with the low-resolution CT images as the input and obtaining the locations of each organ.

9. The apparatus for automatic thoracic organ segmentation according to claim 7, building the two-stage deep learning framework comprises:
cropping the CT images based on the localization CNN output and using the cropped images as the input for organ specific CNN.

10. The apparatus for automatic thoracic organ segmentation according to claim 7, adapting the deep learning framework to be compatible with incomplete training data comprises:
using a modified cross entropy loss function and a modified Dice loss function to adapt the deep learning framework with incomplete training data.

11. The apparatus for automatic thoracic organ segmentation according to claim 7, improving the CNNs upon arrival of new training data comprises:
merging the new data with the old training data and using a transfer learning approach to update the CNNs.

12. The apparatus for automatic thoracic organ segmentation according to claim 7, post-processing the output from the deep learning framework to obtain final organ segmentation comprises:
merging the output from different organ specific CNNs and resolving the conflicts based on the probabilities.

13. A non-transitory computer-readable storage medium having stored therein instructions that, when executed by one or more processors of an apparatus causing the apparatus to perform acts comprising:
receiving three-dimensional (3D) images obtained by a computed tomography (CT) system;
processing the 3D images to have the same spatial resolution and matrix size; building a two-stage deep learning framework using convolutional neural networks (CNNs) for organ segmentation;
adapting the deep learning framework to be compatible with incomplete training data; improving the CNNs upon arrival of new training data;
post-processing the output from the deep learning framework to obtain final organ segmentation;
receiving 3D images and their corresponding information such as pixel spacing, slice thickness and matrix size;
resizing the 3D images to have the same pixel spacing, matrix size; and
applying lower and upper thresholds on the image intensities.

* * * * *